United States Patent [19]

Henning et al.

[11] Patent Number: 4,849,524

[45] Date of Patent: Jul. 18, 1989

[54] PROCESS OF PREPARING PROLINE DERIVATIVES

[75] Inventors: Rainer Henning, Hattersheim am Main; Hansjörg Urbach, Kronberg, both of Fed. Rep. of Germany

[73] Assignee: Hoechst Aktiengesellschaft, Fed. Rep. of Germany

[21] Appl. No.: 122,380

[22] Filed: Nov. 19, 1987

[30] Foreign Application Priority Data

Nov. 21, 1986 [DE] Fed. Rep. of Germany ....... 3639879

[51] Int. Cl.⁴ .................. C07D 207/16; C07D 209/18; C07D 209/54

[52] U.S. Cl. ...................................... 548/411; 544/63; 544/71; 544/72; 548/408; 548/452; 548/492; 548/532; 548/535

[58] Field of Search ............... 548/408, 411, 452, 492, 548/532, 535

[56] References Cited

U.S. PATENT DOCUMENTS 4,691,022 10/1987 Henning et al. .................... 548/408

FOREIGN PATENT DOCUMENTS 132580 2/1985 European Pat. Off. .

*Primary Examiner*—Richard L. Raymond
*Attorney, Agent, or Firm*—Finnegan, Henderson, Farabow, Garrett & Dunner

[57] ABSTRACT

The invention relates to a process for preparing compounds of the formula I

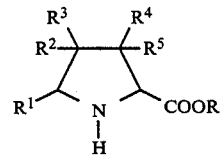

in which R stands for hydrogen, alkyl or aralkyl and $R^1$ to $R^5$ are identical or different radicals, (substituted) alkyl, cycloalkyl or (substituted) aryl or in which the pairs of radicals $R^1$ and $R^2$, $R^2$ and $R^3$, and $R^4$ and $R^5$ together with the carbon atom(s) supporting them form a mono- or bicyclic ring system and the other radicals are hydrogen, by treating a compound of the formula II

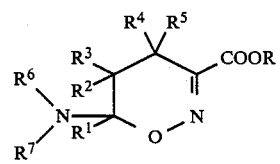

in which R and $R^1$ and $R^5$ have the abovementioned meaning and $R^6$ and $R^7$ denote alkyl or aralkyl or together with the nitrogen atom supporting them form a heterocycle which can additionally contain an oxygen atom, with a reducing agent.

5 Claims, No Drawings

PROCESS OF PREPARING PROLINE DERIVATIVES

DESCRIPTION

Proline derivatives of the formula I are known from the literature. A process for their preparation is described EP-A No. 132,580.

Surprisingly, there has now been found a process for preparing proline derivatives which is distinguished in particular by being simple to carry out.

The invention relates to a process for preparing compounds of the formula I

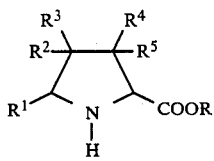

in which

R stands for hydrogen, $(C_1-C_6)$-alkyl or $(C_7-C_9)$aralkyl, and $R^1$ to $R^5$ are identical or different and independently of one another denote hydrogen, $(C_1-C_8)$-alkyl, $(C_3-C_9)$-cycloalkyl, $(C_3-C_9)$-cycloalkyl-$(C_1(C_4)$-alkyl, $(C_5-C_9)$-cycloalkenyl-$(C_1-C_4)$-alkyl, $(C_6-C_{12})$-aryl-$(C_1-C_4)$-alkyl or $(C_6-C_{12})$-aryl, where the two lastmentioned substituents can each be mono-, di- or trisubstituted in the aryl moiety by $(C_1-C_4)$-alkyl, $(C_1-C_4)$-alkoxy, hydroxyl, halogen, nitro, methylenedioxy and/or cyano, or in which the pairs of radicals $R^1$ and $R^2$, $R^2$ and $R^3$, and $R^4$ and $R^5$ together with the carbon atom or two carbon atoms supporting them form a 4-to 10-membered saturated or unsaturated mono- or bicyclic carbocyclic ring system and the other radicals are hydrogen, which comprises treating a compound of the formula II

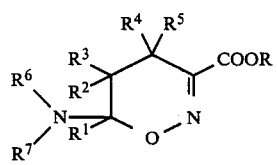

in which

R and $R^1$ to $R^5$ are identical or different and have the abovementioned meaning, and $R^6$ and $R^7$ denote $(C_1-C_6)$-alkyl or $(C_7-C9)$-aralkyl or $R^6$ and $R^7$ together with the nitrogen atom supporting them form a 5- to 10-membered heterocycle which can additionally contain an oxygen atom, with a reducing agent.

Suitable reducing agents are: hydrogen in the presence of a catalyst such as palladium black, palladium on active carbon, platinum on active carbon, rhodium on active carbon, Raney nickel or Raney cobalt in a lower alcohol (such as $(C_1-C_4)$-alkanol) or a lower carboxylic acid (such as formic acid, acetic acid, propionic acid or butyric acid) with or without addition of a mineral acid such as, for example, hydrochloric acid, hydrobromic acid or sulfuric acid and also sodium borohydride, sodium cyanoborohydride, sulfited sodium borohydride ($NaBH_2S_3$), borane/dimethyl sulfide, borane/pyridine, borane/trimethylamine, sodium dithionite, sodium in a lower alcohol (such as $(C_1-C_4$-alkanol), sodium amalgam or aluminum amalgam, but preferably reducing agents such as hydrogen in the presence of catalysts such as palladium black, palladium on active carbon, platinum on active carbon, rhodium on active carbon, Raney nickel or Raney cobalt.

The synthesis can be carried out between $-20°$ C. and the boiling point of the reaction mixture, preferably between 20° C. and 60° C. The $H_2$ pressure in the reaction is $1 \times 10^5$ to $2 \times 10^7$ N m$^{-2}$, preferably $1 \times 10^5$ to $5 \times 10^6$ N m$^{-2}$.

A preferred embodiment comprises preparing compounds of the formula I in which

R has the abovementioned meaning, $R^1$ to $R^5$ are identical or different and independently of one another denote hydrogen, methyl, ethyl, propyl, isopropyl, tert.butyl, n-pentyl, cyclopentyl, cyclohexyl, cycloheptyl, cyclopentylmethyl, cyclopentylethyl cyclohexylmethyl, phenyl, naphthyl, 4-methoxyphenyl, 4-fluorophenyl, 4-chlorophenyl, 3,4-dimethoxy phenyl, 3,4-methylenedioxyphenyl, 3,4-dichlorophenyl, p-tolyl, benzyl, 4-methoxybenzyl, 4-chlorobenzyl, phenethyl, 2-phenylpropyl or 1-phenylpropyl or in which the pairs of radicals $R^1$ and $R^2$, $R^2$ and $R^3$, and $R^4$ and $R^5$ form in the above-defined manner a cyclobutane, cyclopentane, cyclohexane, cycloheptane, cyclooctane, bicyclo[2.2.1]heptane or bicyclo[2.2.2]octane ring, the remaining radicals being hydrogen.

Particular preference is given to an embodiment which comprises preparing compounds of the formula I in which R has the abovementioned meaning, but denotes in particular hydrogen, tert.butyl or benzyl, and in which one or two of the radicals $R^1$ to $R^5$ independently of each other denote methyl, ethyl, propyl, isopropyl, npentyl, cyclopentyl, cyclohexyl, phenyl, 4-methoxyphenyl, 4-fluorophenyl, benzyl, phenethyl or 4-methoxybenzyl and the others denote hydrogen, or the pairs of radicals $R^1$ and $R^2$, and $R^2$ and $R^3$ together with the carbon atom or two carbon atoms supporting them form a cyclopentane, cyclohexane, cycloheptane, bicyclo[2.2.1] heptane or bicyclo[2.2.2] octane ring, the other radicals denoting hydrogen.

The process according to the invention produces the compounds of the formula I as mixtures of enantiomers or diastereoisomers or as pure diastereoisomers, depending on the way the process is carried out and the nature of the substituents $R^1$ to $R^5$. The resulting mixtures can be separated into their constituents by suitable methods known per se, such as fractional crystallization or chromatography in the case of diastereoisomers, or the formation of diastereoisomeric salts, if desired of suitable derivatives, in the case of enantiomeric mixtures.

The process according to the invention is very particularly advantageous for preparing the following compounds of the formula I.

ethyl cis-octahydro[1H]indole-2-exo-carboxylate
ethyl cis-octahydro[1H]indole-2-endo-carboxylate
ethyl trans-octahydro[1H]indole-2-α-carboxylate
ethyl trans-octahydro[1H]indole-2-β-carboxylate
ethyl cis-octahydrocyclopenta[b]pyrrole-2-exo-carboxylate
ethyl cis-octahydrocyclopenta[b]pyrrole-2-endo-carboxylate
ethyl trans-octahydrocyclopenta[b]pyrrole-2-α-carboxylate
ethyl trans-octahydrocyclopenta[b]pyrrole-2-β-carboxylate ethyl 2-azaspiro[4,5]decane-3-carboxylate
ethyl 2-azaspiro[4,4]nonane-3-carboxylate
ethyl spiro[bicyclo[2.2.2]octane-2,3'-pyrrolidine]-5-exo carboxylate
ethyl spiro[bicyclo[2.2.2]octane-2,3'-pyrrolidine]-5-endo carboxylate
ethyl spiro[bicyclo[2.2.1]heptane-2,3'1 -pyrrolidine]-5-exocarboxylate
ethyl cis-exo-3-azatricyclo[5.2.1.0$^{2.6}$]decane-4-exocarboxylate
ethyl cis-exo-3-azatricyclo[5.2.1.0$^{2.6}$]decane-4-endocarboxylate
ethyl cis-endo-3-azatricyclo[5.2.1.0.$^{2.6}$]decane-4-endocarboxylate
ethyl cis-endo-3-azatricyclo[5.2.1.0.$^{2.6}$]decane-4-exocarboxylate
ethyl cis-decahydrocyclohepta[b]pyrrole-2-exo-carboxylate
ethyl cis-decahydrocyclohepta[b]pyrrole-2-endo-carboxylate
ethyl trans-decahydrocyclohepta[b]pyrrole-2-α-carboxylate
ethyl trans-decahydrocyclohepta[b]pyrrole-2-β-carboxylate
ethyl 1-aza-spiro[4,5]decane-2-carboxylate
ethyl 1-aza-spiro[4,4]nonane-2-carboxylate
ethyl ester of 4,5-cis-diethylproline
ethyl ester of 4,5-cis-dimethylproline
ethyl ester of 5,5-dimethylproline
ethyl ester of 4,4-dimethylproline
ethyl ester of 4,4-diethylproline
ethyl ester of 3,3-dimethylproline
ethyl ester of 4,5-cis-diphenylproline
ethyl ester of 4-phenylproline
and the corresponding free acids.

Compounds of the formula I in which R is ($C_1$–$C_6$)-alkyl or ($C_7$–$C_9$)-aralkyl can be converted in a manner known per se under hydrogenolytic, acid or basic conditions, for example wih mineral acid such as hydrochloric acid, hydrobromic acid or sulfuric acid, at 0° to 150° C., preferably at 60° to 120° C., or with hydrogen in the presence of a transition metal catalyst, for example Raney nickel or palladium on active carbon, into compounds of the formula I in which R is hydrogen. J. Chem. Soc. Chem. Commun 1979, 1089 describes the preparation of a compound of the formula II in which R is ethyl, $R^1$ and $R^2$ together form a —[$CH_2$]$_4$—chain, $R^3$ to $R^5$ stand for hydrogen and $R^6$ and $R^7$,together with the nitrogen atom supporting them, stand for a morpholine ring. Further reactions are not disclosed.

With the exception of this said compound, the compounds of the formula II are novel and likewise form part of the subject-matter of the invention.

The invention further relates to a process for preparing compounds of the formula II, which comprises reacting a compound of the formula III

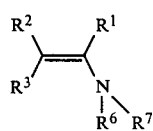
III with a compound of the formula IV

IV in which

R stands for hydrogen, ($C_1$–$C_6$)-alkyl or ($C_7$–$C_9$)-aralkyl, $R^1$ to $R^5$ are identical or different and independently of one another denote hydrogen, ($C_1$–$C_8$)-alkyl, ($C_3$–$C_9$)-cycloalkyl, ($C_3$–$C_9$)-cycloalkyl-($C_1$–$C_4$)-alkyl, ($C_5$–$C_9$)-cycloalkenyl-($C_1$–$C_4$)-alkyl, ($C_6$–$C_{12}$)-aryl-($C_1$–$C_4$)-alkyl or ($C_6$–$C_{12}$)-aryl, where the two last mentioned substituents can each be mono-, di- or trisubstituted in the aryl moiety by ($C_1$–$C_4$)-alkyl, ($C_1$–$C_4$)-alkoxy, hydroxyl, halogen, nitro, methylenedioxy and/or cyano, or in which pairs of radicals $R^1$ and $R^2$, $R^2$ and $R^3$, and $R^4$ and $R^5$ together with the carbon atom or two carbon atoms supporting them form 4-to a 10-membered saturated or unsaturated mono- or bicyclic carbocyclic ring system and the other radicals are hydrogen, $R^6$ and $R^7$ denote ($C_1$–$C_4$)-alkyl or ($C_7$–$C_9$)-aralkyl or $R^6$ and $R^7$, together with the nitrogen atom supporting them, form a 5-to 10-membered heterocycle which can additionally contain an oxygen atom, and X denotes chlorine or bromine.

The reaction is carried out in an aprotic organic solvent, preferably an ether such as, for example, diethyl ether, diisopropyl ether, tetrahydrofuran or dioxane or a chlorinated hydrocarbon such as, for example, dichloromethane or chloroform in the presence of a weak base such as, for example, sodium hydrogencarbonate, sodium carbonate, potassium carbonate or a trialkylamine or pyridine within a temperature range of −40° C. to 100° C., preferably 0° C. to 50° C.

The compounds of the formula III are known from G. Cook, Enamines (Marcel Decker, New York and London, 1969). Compounds of the formula IV are obtained from compounds of the formula V

V in which R, $R^4$, $R^5$ and X are as defined above, by reaction with hydroxylamine, as described in J. Chem. Soc. Commun 1979, 1089.

The compounds of the formula I are useful intermediates in the preparation of pharmaceuticals, in particular in the preparation of inhibitors of angiotensin converting enzyme (ACE). Compounds of this type are known for example from EP-A-No.50,800 or also form part of the subject matter of German Pat. application No. 31 51 690.4. These ACE-inhibitors are for example substituted acyl derivatives of the formula VI

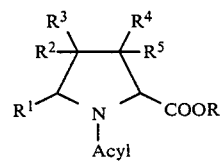
VI in which R, $R^1$ to $R^3$ are as defined above, $R^4$ and $R^5$ denote hydrogen, and acyl stands for example for a radical of the formula VII

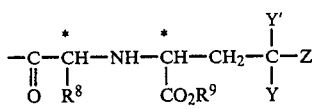

in which $R^8$ denotes hydrogen, $(C_1-C_6)$-alkyl, which may be substituted by amino, $(C_1-C_4)$-acylamino or benzoylamino, $(C_2-C_6)$-alkenyl, $(C_5-C_9)$-cycloalkyl, $(C_5-C_9)$-cycloalkenyl, $(C_5-C_7)$-cycloalkyl-$(C_1-C_4)$-alkyl, aryl or partially hydrogenated aryl which can each be substituted by $(C_1-C_2)$-alkyl, $(C_1-C_2)$-alkoxy or halogen, aryl-$(C_1-C_4)$-alkyl whose aryl radical can be substituted as defined above, a mono- or bicyclic heterocyclic radical having 5 to 7 or 8 to 10 ring atoms, of which 1 to 2 ring atoms represent sulfur or oxygen atoms and/or of which 1 to 4 ring atoms represent nitrogen atoms, or denotes a side chain of an amino acid, $R^9$ denotes hydrogen, $(C_1-C_6)$-alkyl, $(C_2-C_6)$-alkenyl or aryl-$(C_1-C_4)$-alkyl, Y and Y' are hydrogen or together oxygen, Z denotes $(C_1-C_6)$-alkyl, $(C_2-C_6)$-alkenyl, $(C_5-C_9)$-cycloalkyl, aryl which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$ -alkylamino and/or methylenedioxy, or denotes indol-3-yl, and their physiologically safe salts.

Compounds of the formula VI can be prepared for example by N-acylation of suitable esters of compounds of the formula I, such as, for example, benzyl or tert.-butyl esters with compounds of the formula acyl-OH, in which acyl is as defined above, and subsequent hydrogenolytic, acid or basic elimination of the ester groups.

The condensation of esters of the compounds of formula I with compounds of the formula acyl-OH is preferably effected by known methods of peptide chemistry. Particular preference is given to those methods which afford sufficient protection against racemization, such as, for example, the DCC/HOBt method or the alkanephosphonic anhydride method described in U.S. Pat. 4,331,592.

The compounds of the formula VI have an intensive and prolonged hypotensive action. They are readily absorbed after peroral administration and can be used for controlling blood hypertension of various origins and be employed by themselves or combined with other hypotensive, vasodilating or diuretically active compounds. They can be administered intravenously, subcutaneously or perorally, peroral administration being preferred. The dosage in peroral administration is in general from 0.01 to 10 mg/kg per day.

The dose can even be increased in serious cases, since toxic properties have hitherto not been observed. It is also possible to reduce the dose, which is advisable in particular when diuretics are administered at the same time. In the case of intravenous and subcutaneous administration, the individual dose should be between 0.1 and 250 µg/day.

The Examples which follow are intended to illustrate the invention without limiting it to the Examples described.

EXAMPLE 1

Ethyl cis-octahydro[1H]-indol-2-carboxylate (a) Ethyl 8a-morpholino-1-oxa-2-aza-1,4,4a,5,6,7,8,8a-octahydronaphthalene-3-carboxylate 5 g (30 mmol) of morpholinocyclohexene and 1.9 g (10 mmol) of ethyl 3-bromo-2-hydroxyiminopropionate are stirred at room temperature together with 2 g of potassium carbonate in 80 ml of dichloromethane for 4 hours. Filtration is followed by concentrating and chromatography over silica gel (eluant: ethyl acetate/cyclohexane 1:4). 2.1 g of a colorless oil are obtained.

$^1$H-NMR (CDCl$_3$): δ=4.3 (q,2H), 3.6 (t,4H), 2.8 (m, 2H), 2.6 (m,2H), 2.3 (m,2H), 1.4 (t,3H), 1.7 - 1.0 (m,9H) ppm.

(b) Ethyl cis-octahydro[1H]indol-2-carboxylate 2.1 g of the product of Example 1(a) are hydrogenated at 50° C. under atmospheric pressure in 60 ml of ethanol using 0.5 g of Raney nickel in the course of 4 hours. 1.3 g of ethyl cis-octahydro[1H]indol-2-carboxylate are obtained as a pale yellow oil after filtration and concentrating in vacuo.

EXAMPLE 2

Methyl cis-2-aza-bicyclo[3.3.0]octane-3-carboxylate (a) Methyl 1-morpholino-2-oxa-3-aza-bicyclo[4.3.0]non-3-ene-4-carboxylate 4.6 g (30 mmol) of morpholinocyclopentane are reacted with 1.75 g (10 mmol) of methyl 3-bromohydroxyiminopropionate by following the method of Example 1(a). 1.9 g of a colorless oil are obtained.

$^1$H-NMR (CDCl$_3$):δ=3.8 (s,3H), 3.6 (t,4H), 2.8 (m, 2H), 2.6 (m,2H), 2.3 (m,2H), 1.7–1.0 (m,3H) ppm.

(b) Methyl cis-2-aza-bicyclo[3.3.0]octane-3-carboxylate

The method of Example 1b) is followed to convert 1.9 g of methyl 1-morpholino-2-oxa-3-aza-bicyclo[4.3.0]non-3- ene-4-carboxylate into 1.0 g of methyl cis-2-aza-bicyclo[3.3.0]octane-3-carboxylate in the form of a pale yellow oil. Example 3

Ethyl spiro[bicyclo[2.2.2]octane-2,3'-pyrrolidine]-5'-carboxylate (a) Spiro[bicyclo[2.2.2]octane-2,5'-(6'-pyrrolidino)-4'H 5',6'-dihydro-1',2'-oxazine]

4.5 g (20 mmol) of 2-pyrrolidinomethylenebicyclo[2.2.2]octane and 2.75 g (13 mmol) of ethyl 3-bromo-2-hydroxyiminopropionate are dissolved in 50 ml of dichloromethane. 5 g of sodium carbonate are then added and stirred in at 25oC for 2 hours. Filtration is followed by concentrating. Chromatography over silica gel using ethyl acetate/cyclohexane (1:8) as an eluant gives 2.45 g of product. Melting point 116-118oC (n-hexane)

$^1$H-NMR (CDCl$_3$): δ=4.95 +4.85 (2d,1H), 4.3 (2q,2H), 3.0 (m,2H), 2.7 (m,2H), 2.6 +2.2 (AB system,2H), 1.9 - 1.4 (m,16H), 1.4 (t,3H) ppm.

(b) Ethyl spiro[bicyclo[2.2.2]octane-2,3'-pyrrolidine]-5' carboxylate 2.4 g of the product of Example 3(a) are hydrogenated in 60 ml of ethanol using 0.4 g of Raney nickel by following the method described in Example 1b). This gives 1.9 g of a pale yellow oil which contains the two diastereoisomers (S*,S* and S*,R*) in a ratio of 3:1. The isomers can be separated after acetylation with acetyl chloride/triethylamine in tetrahydrofuran.

Isomer 1 (S,S): 0.5 g, melting point 122° C. $^1$H–NMR (CDCl$_3$ : δ=4.4 (m,1H), 4.2 (q,2H), 3.9 –3.1 (m,1H), 2.4 –1.8 (m,1H), 2.1 +
1.95 (2s,3H), 1.7 –1.3 (m,13H),
1.25 (t,3H) ppm.

Isomer 2 (S,R): 1.5 g, oil.
$^1$H-NMR (CDCl$_3$):δ=4.5–4.3 (m,1H), 4.3–4.1 (m, 2H), 3.6–3.3 (m,2H), 2.4–1.8 (m,2H), 2.1+1.95 (2s,3H), 1.8 –1.3 (m,12H), 1.3 (t,3H) ppm.

EXAMPLE 4

Ethyl ester of 4,4-pentamethyleneproline (a)

3-Ethoxycarbonyl-5,5-pentamethylene-6-pyrrolidino-4H-5,6-dihydro-1,2-oxazine 3.3 g (20 mmol) of pyrrolidinomethylenecyclohexane are reacted with 2.75 g (13 mmol) of ethyl 3-bromo-2-hydroxyiminopropionate by following the method of Example 3(a). 1.6 g of 3-ethoxycarbonyl-5,5-pentamethylene-6-pyrrolidino-4H-5,6-dihydro-1,2-oxazine are obtained in the form of an oil.

$^1$H-NMR CDCl$_3$): δ=4.9 (s,1H), 4.3 (2q,2H), 3.0 (m,2H), 2.7 (m,2H), 2.6 +2.2 (AB system,2H), 1.9–1.4 (m,14H), 1.4 (t,3H) ppm.

(b) Ethyl ester of 4,4-pentamethyleneproline 1.6 g of the product of Example 4a) are hydrogenated using 0.2 g of Raney nickel by following the method given in Example 1b). 0.9 g of a pale yellow oil is obtained.

$^1$H-NMR (CDCl$_3$):δ=4.2 (q,2H), 3.9 (m,1H), 3.4 (m,2H), 1.9–1.3 (m,12H), 1.25 (t,3H) ppm.

We claim:
1. A process for preparing compounds of the formula I

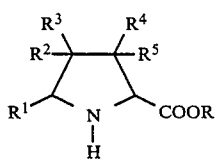

in which
R stands for hydrogen, ($C_1$-$C_6$)-alkyl or ($C_7$-$C_9$)aralkyl, and
$R^1$ to $R^5$ are identical or different and independently of one another denote hydrogen, ($C_1$-$C_8$)-alkyl, ($C_3$-$C_9$)-cycloalkyl, ($C_3$-$C_9$)-cycloalkyl-($C_1C_4$)-alkyl, ($C_5$-$C_9$)-cycloalkenyl-($C_1$-$C_4$)-alkyl, ($C_6$-$C_{12}$)-aryl-($C_1$-$C_4$)-alkyl or ($C_6$-$C_{12}$)-aryl, where the two lastmentioned substituents can each be mono-, di- or trisubstituted in the aryl moiety by ($C_1$-$C_4$)-alkyl, ($C_1$-C4)-alkoxy, hydroxyl, halogen, nitro, methylenedioxy and/or cyano, or in which the pairs of radicals $R^1$ and $R^2$,$R^2$ and $R^3$, and $R^4$ and $R^5$ together with the carbon atom or two carbon atoms supporting them form a 4- to 10- membered saturated or unsaturated mono- or bicyclic carbocyclic ring system and the other radicals are hydrogen,
which comprises treating a compound of the formula II

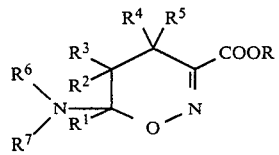

in which
R and $R^1$ to $R^5$ are identical or different and have the abovementioned meaning, and
$R^6$ and $R^7$ denote ($C_1$-$C_6$)-alkyl or ($C_7$-$C_9$)-aralkyl or
$R^6$ and $R^7$ together with the nitrogen atom supporting them form a 5- to 10-membered heterocycle which can additionally contain an oxygen atom,
with a reducing agent and if desired converting the product under hydrogenolytic, acid or basic conditions into compounds of the formula I in which R is hydrogen.

2. The process as claimed in claim 1, wherein R is defined as in claim 1,
$R^1$ to $R^5$ are identical or different and independently of one another denote hydrogen, methyl, ethyl, propyl, isopropyl, tert.butyl, n-pentyl, cyclopentyl, cyclohexyl, cycloheptyl, cyclopentylmethyl, cyclopentylethyl, cyclohexylmethyl, phenyl, naphthyl, 4-methoxyphenyl, 4-fluorophenyl, 4-chlorophenyl, 3,4-dimethoxyphenyl, 3,4-methylenedioxyphenyl, 3,4-dichlorophenyl,p-tolyl, benzyl, 4-methoxybenzyl, 4-chlorobenzyl, phenethyl, 2-phenylpropyl or 1-phenylpropyl
or in which the pairs of radicals $R^1$ and $R^2$,$R^2$ and $R^3$,and $R^4$ and $R^5$ form in the above-defined manner a cyclobutane, cyclopentane, cyclohexane, cycloheptane, cyclooctane, bicyclo- 2.2.1]heptane or bicyclo[2.2.2]octane ring, the remaining radicals being hydrogen.

3. The process as claimed in claim 1, wherein R is as defined in claim 1, but denotes in particular hydrogen, tert.-butyl or benzyl, and in which one or two of the radicals $R^1$ to $R^5$ independently of each other denote methyl, ethyl, propyl, isopropyl, n-pentyl, cyclopentyl, cyclohexyl, phenyl, 4-methoxyphenyl, 4-fluorophenyl, benzyl, phenethyl or 4-methoxybenzyl and the others denote hydrogen, or the pairs of radicals $R^1$ and $R^2$, and $R^2$ and $R^3$ together with the carbon atom or two carbon atoms supporting them form a cyclopentane, cyclohexane, cycloheptane, bicyclo[2.2.1]-heptane or bicyclo[2.2.2]octane ring, the other radicals denoting hydrogen.

4. The process as claimed in claim 1 for preparing ethyl spiro[bicyclo[2.2.2]octane-2,3'-pyrrolidine]-5'-carboxylate.

5. The process as claimed in claim 1, wherein the reducing agent used is hydrogen in the presence of a catalyst such as palladium black, palladium on active carbon, platinum on active carbon, rhodium on active carbon, Raney nickel or Raney cobalt, sodium borohydride, sodium cyanoborohydride, sulfited sodium borohydride (NaBh$_2$S$_3$), borane/dimethyl sulfide, borane/pyridine, borane/trimethylamine, sodium dithionite, sodium in a lower alcohol, sodium amalgam or aluminum amalgam.

* * * * *

UNITED STATES PATENT AND TRADEMARK OFFICE
CERTIFICATE OF CORRECTION

PATENT NO.  : 4,849,524

DATED       : July 18, 1989

INVENTOR(S) : Rainer Henning, Hansjorg Urbach

It is certified that error appears in the above-identified patent and that said Letters Patent is hereby corrected as shown below:

Claim 1, col. 7, line 54, change "($C_7$-$C_9$)aral-" to -- ($C_7$-$C_9$)-aral- --;

Claim 1, col. 7, line 58, change "($C_1 C_4$)" to -- ($C_1$-$C_4$) --;

Claim 1, col. 7, line 63, change "C4" to -- $C_4$ --;

Claim 1, col. 7, line 65, change "the pairs" to -- a pair --; and change "and $R^4$" to -- or $R^4$ --;

Claim 1, col. 7, line 67, change "form" to -- forms --; and

Claim 1, col. 7, line 68, change "unsaturated" to -- unsaturated --.

Claim 2, col. 8, line 37, change "the pairs" to -- a pair --;

Claim 2, col. 8, line 38, change "and $R^4$" to -- or $R^4$ --; and change "form" to -- forms --; and Claim 2, col. 8, line 40, change "bicyclo-" to -- bicyclo[ --.

Claim 3, col. 8, line 49, change "the pairs" to -- a pair --; and change "$R^2$, and" to -- $R^2$, or --.

Claim 5, col. 8, line 64, change "($NaBh_z S_3$)" to -- ($NaBH_2 S_3$) --.

Signed and Sealed this

Tenth Day of July, 1990

Attest:

HARRY F. MANBECK, JR.

Attesting Officer

Commissioner of Patents and Trademarks